United States Patent [19]

Schumann

[11] Patent Number: Plant 7,394

[45] Date of Patent: Dec. 11, 1990

[54] GERANIUM PLANT NAMED FISGLO

[75] Inventor: Ingeborg Schumann, Hoehr-Grenzhausen, Fed. Rep. of Germany

[73] Assignee: Florfis AG, Binningen, Switzerland

[21] Appl. No.: 426,175

[22] Filed: Oct. 25, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of Geranium plant named Fisglo, particularly characterized by the combined features of bright orange semi-double flowers, without burning of petals in the sun, early flowering, compact habit and medium green foliage.

1 Drawing Sheet

The present invention comprises a new and distinct cultivar of Geranium, botanically known as *Pelargonium zonale,* and hereinafter referred to by the cultivar name Fisglo.

Fisglo is a product of a planned breeding program which had the objective of creating new geranium cultivars with orange-red semi-double flowers, good branching, better chlorophyll quality for better transportation, better temperature tolerance, and fast rooting.

Fisglo was originated from a hydridization made by the inventor in a controlled breeding program in Galdar, Gran Canaria, Spain, in 1983.

The female parent was an inbred line of the cultivar Achspen, characterized by its early flowering, fast rooting and very good branching. The male parent of Fisglo was the cultivar Silvia Maria, characterized by its orange semi-double flowers, tall habit, and inferior rooting habit.

Fisglo was discovered and selected as one flowering plant within the progeny of the stated cross by Ingeborg Schumann in May 1984 in a controlled environment in Galdar, Gran Canaria, Spain.

The first act of asexual reproduction of Fisglo was accomplished when vegetative cuttings were taken from the initial selection in February 1985 in a controlled environment in Hillscheid, Federal Republic of Germany by, or under the supervision of, Ingeborg Schumann.

Horticultural examination of selected units initiated in Spring 1985 and continuing thereafter has demonstrated that the combination of characteristics as herein disclosed for Fisglo are firmly fixed and are retained through successive generations of asexual reproduction.

Fisglo has not been observed under all possible environmental conditions. The phenotype may vary significantly with variations in environment such as temperature, light intensity and daylength.

The following observations, measurements and comparisons describe plants grown in Hillscheid, Federal Republic of Germany, under greenhouse and outdoor conditions which approximate those generally used in commercial practice.

The following traits have been repeatedly observed and are determined to be basic characteristics of Fisglo, which, in combination, distinguish this Geranium as a new and distinct cultivar:

1. Orange-red flowers.

2. Semi-double flower form.
3. Medium zonation.
4. Early flowering.
5. Fast rooting.
6. Good branching.
7. Temperature tolerance.
8. Good chlorophyll for better transportation.

Of the many commercial cultivars known to the present inventor, the most similar in comparison to Fisglo is the cultivar Casino, disclosed in U.S. Plant Pat. No. 5,938. Reference is made to attached Chart A which compares certain characteristics of Fisglo to those same characteristics of Casino. In general comparison to Casino, Fisglo has, among other things, better branching, faster rooting, a lighter, less reddish shade of orange color, and a more compact habit.

The accompanying color photographic drawing shows typical flower and foliage characteristics of Fisglo, with the colors being as true as possible with illustrations of this type.

In the following description color references are made to The Royal Horticultural Society Colour Chart. The color values were determined between 2:00 p.m. and 3:00 p.m. indoors on May 13, 1988 under 45,000 Lux light intensity at Hillscheid, Federal Republic of Germany.

Classification:

*Botanical.*—A hybrid of the genus *Pelargonium zonale* l'hert. cv Fisglo.

*Commercial.*—Zonal geranium.

INFLORESCENCE

A. Umbel:

*Average diameter.*—Indoor, 9.2 cm; outdoor, 8.9 cm.

*Average depth.*—Indoor, 4.5 cm; outdoor, 4.6 cm.

*Peduncle length.*—Indoor, 13.5 cm; outdoor, 11.0 cm.

*Pedicel length.*—Indoor, 2.4 cm; outdoor, 2.3 cm.

B. Corolla:

*Average diameter.*—Indoor, 4.3 cm; outdoor, 4.3 cm.

*Form.*—Semi-double.

*Color (general tonality from a distance of three meters).*—Orange-red, 41B; color fades to pink when flowers wilt.

*Color (main body, upper surface).*—Between 41A and 43B.

*Color (near margin).*—RHS 43C.

*Lower side of petal.*—More reddish, 47C.

C. Bud:

*Shape.*—Elliptic.

*Color.*—Light green.

*Sepals and pedicel.*—Light green.

D. Reproductive organs:

*Androecium.*—6–8 anthers.

*Gynoecium.*—5 lobed stigma.

E. Spring flowering response period: In Hillscheid, Federal Republic of Germany in 1988, 80% of plants with at least 1 flower opened 11 weeks after planting of unrooted cuttings in February.

F. Outdoor flower production: The flower count in 1988 in Hillscheid, Federal Republic of Germany indicated between 42 and 48 flowers per plant for June through October observation period.

G. Durability: Medium weather resistance.

PLANT

A. Foliage:

*Form.*—Kidney shaped.

*Margin.*—Bicrenate.

*Color.*—Medium green.

*Zonation.*—Weak, brown zonation.

*Tolerance to botrytis.*—Medium to good.

B. General appearance and form:

*Internode length.*—Medium to short.

*Branching pattern.*—5.6 branches per plant 13 weeks of growing time from unrooted cuttings.

*Height.*—25 cm on average.

CHART A

COMPARISON OF FISGLO AND CASINO

| | FISGLO | CASINO |
|---|---|---|
| Chlorophyll quality | good | medium |
| Flower color | orange | orange-red |
| Color of lower side | lighter orange with white spots | light rose, almost white |
| Durability, shatter resistance | very good | good |
| Pedicels | light green | green with anthocyan |
| Peduncles | short | long |
| Low temperature tolerance | good | medium |
| Salt tolerance | medium | good |
| Plant habit | compact | tall |
| Branching habit (number of branches) | 5.6 | 6.0 |
| Beginning of flowering | early-medium | medium |

I claim:

1. A new and distinct cultivar of Geranium plant named Fisglo, as illustrated and described.

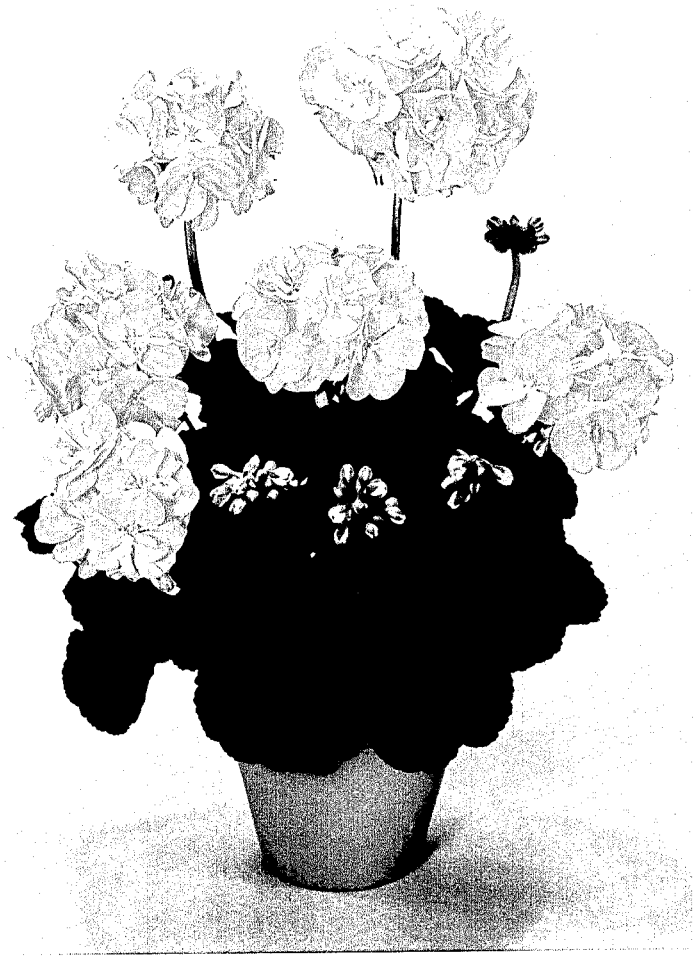

* * * * *